(12) United States Patent
Prien et al.

(10) Patent No.: US 6,519,954 B1
(45) Date of Patent: Feb. 18, 2003

(54) CRYOGENIC PRESERVATION OF BIOLOGICALLY ACTIVE MATERIAL USING HIGH TEMPERATURE FREEZING

(75) Inventors: Samuel D. Prien, Lubbock, TX (US); John Blanton, Lubbock, TX (US); Kevin R. Pond, Lubbock, TX (US); Markus F. Miller, Lubbock, TX (US); Brian Wood, Melbourne (AU); Allan J. Cassell, Melbourne (AU)

(73) Assignee: Supachill International Pty. Ltd., West Heidelberg (AT)

( * ) Notice: Subject to any disclaimer, the term of this patent is extended or adjusted under 35 U.S.C. 154(b) by 0 days.

(21) Appl. No.: 09/655,807

(22) Filed: Sep. 6, 2000

Related U.S. Application Data (60) Provisional application No. 60/210,913, filed on Jun. 12, 2000.

(51) Int. Cl.[7] .................................................. F17B 17/02
(52) U.S. Cl. ................................................. 62/64; 62/78
(58) Field of Search ........................................ 62/64, 78

(56) References Cited

U.S. PATENT DOCUMENTS

| | | | | |
|---|---|---|---|---|
| 4,429,542 A | * | 2/1984 | Sakao et al. ................... | 62/78 |
| 4,676,070 A | * | 6/1987 | Linner ........................... | 62/64 |
| 4,848,094 A | * | 7/1989 | Davis et al. ................... | 62/64 |
| 5,003,787 A | | 4/1991 | Zlobinsky .................... | 62/185 |
| 5,191,773 A | | 3/1993 | Cassell ......................... | 62/373 |
| 5,222,367 A | * | 6/1993 | Yamada ......................... | 62/64 |

FOREIGN PATENT DOCUMENTS

| | | | |
|---|---|---|---|
| DE | 1238618 | 4/1967 | |
| WO | WO 91/02202 | 2/1991 | ........... F25D/23/02 |

OTHER PUBLICATIONS

"Rapid Freezing Apparatus For Agricultural Products And Processed Food": European Patent Office, Patent Abstracts of Japan; Yamashita Yuji, Int. Cl. F25D 13/00; Publication No. 02126075; Publication Date: May 15, 1990.

* cited by examiner

*Primary Examiner*—Ronald Capossela
(74) *Attorney, Agent, or Firm*—Simon, Galasso & Frantz PLC; Raymond M. Galasso

(57) ABSTRACT

Viable biological material is cryogenically preserved (cryopreservation) by preparing the material for freezing, immersing the material in a tank of cooling fluid, and circulating the cooling fluid past the material at a substantially constant predetermined velocity and temperature to freeze the material. A method according to the present invention freezes the biologic material quickly enough to avoid the formation of ice crystals within cell structures (vitrification). The temperature of the cooling fluid is preferably between −20° C. and −30° C., which is warm enough to minimize the formation of stress fractures in cell membranes due to thermal changes. Cells frozen using a method according to the present invention have been shown to have approximately an 80 percent survival rate, which is significantly higher than other cryopreservation methods.

54 Claims, 6 Drawing Sheets

CRYOGENIC PRESERVATION OF BIOLOGICALLY ACTIVE MATERIAL USING HIGH TEMPERATURE FREEZING

CROSS REFERENCE TO RELATED APPLICATIONS

This application claims the benefit of United States Provisional Patent Application Serial No. 60/210,913 filed Jun. 12, 2000 entitled "CRYOGENIC PRESERVATION OF BIOLOGICALLY ACTIVE MATERIAL USING HIGH TEMPERATURE FREEZING."

FIELD OF THE INVENTION

The present invention relates generally to cryogenic preservation, and more particularly to cryogenic preservation of biologically active materials using vitrification techniques.

BACKGROUND OF THE INVENTION

Cryogenic preservation (cryopreservation) can be defined as lowering the temperature of living structures and biochemical molecules to the point of freezing and beyond, for the purposes of storage and future recovery of the material in its pre-frozen, viable condition. Experiments with canine sperm in the 1700's first demonstrated that single cells could be frozen and later thawed, and that a small percentage of cells returned to normal physiological function. Later, in the 1900's, it was found that cell recovery rates could be improved if the cells where chemically prepared to withstand the freezing process using compounds collectively referred to as cryoprotectants. However, even with the use of cryoprotectants, recovery rates from cryopreservation are routinely 50 percent or less.

To date attempts to improve cryopreservation recovery rates have generally focused on new cryoprotectants to treat biological material prior to freezing and extremely slow or fast freezing techniques. Both techniques are generally directed towards reducing cellular damage caused when the water within cells expands due to the formation of ice crystals during the freezing process. In theory, extremely slow or fast freezing will reduce or eliminate the formation of ice crystals within a cell. Mechanisms for extremely slow rates of freezing have included controlled descent through nitrogen vapors into liquid nitrogen, or moving samples through super-cooled alcohol compounds followed by plunging into liquid nitrogen. Freezing in this manner does not allow further growth of ice crystal size during the freezing process, but still allows ice crystal formation.

Another technique, often referred to as vitrification, plunges samples directly into liquid nitrogen in an attempt to freeze the water within the cell so rapidly that ice crystal formation is inhibited. Vitrification rapidly takes cells from room temperature to −196° C., the temperature of liquid nitrogen. Such an extreme drop in temperatures in such a short time often causes stress fractures within the cell membrane. Cryoprotectants are used in conjunction with vitrification and various other freezing techniques.

SUMMARY OF THE INVENTION

Therefore, what is needed is an improved way to cryogenically preserve viable single cells, tissues, organs, nucleic acids, or other biologically active molecules, that avoids at least some of the problems inherent in currently available methods. Accordingly, at least one embodiment of the present invention provides a method of cryopreservation comprising immersing biologically active material in cooling fluid and circulating the cooling past the material. The material may or may not undergo chemical preparation prior to immersion, depending on the type of materials being cryopreserved. The cooling fluid is circulated past the material at a substantially constant predetermined velocity and temperature to freeze the material such that the material is vitrified, and the formation of stress fractures in cell membranes is minimized. In at least one embodiment, the cooling fluid is maintained at a temperature of between about −20 degrees centigrade and −30 degrees centigrade, and the velocity of the cooling fluid past the material is about 35 liters per minute per foot of cooling fluid through an area not greater than about 24 inches wide and 48 inches deep. Additionally, at least one embodiment of the present invention freezes the material directly to a temperature higher than about −30 degrees centigrade. Yet another embodiment of the present invention provides a biological material having been subjected to such a cryopreservation process.

An object of at least one embodiment of the present invention is to freeze biological material such that the formation of ice crystals and stress fractures are avoided.

An advantage of at least one embodiment of the present invention is that cryopreservation recovery rates are significantly increased, because biological material is vitrified during freezing.

Another advantage of at least one embodiment of the present invention is that cryopreservation recovery rates are improved, because biological material is vitrified at a high enough temperature to avoid the formation of stress fractures within cell membranes.

A further advantage of at least one embodiment of the present invention is that once frozen, current cryoperservation storage facilities and mechanisms can be used to store the frozen biological material.

BRIEF DESCRIPTION OF THE DRAWINGS

Other objects, advantages, features and characteristics of the present invention, as well as methods, operation and functions of related elements of structure, and the combination of parts and economies of manufacture, will become apparent upon consideration of the following description and claims with reference to the accompanying drawings, all of which form a part of this specification, wherein like reference numerals designate corresponding parts in the various figures, and wherein:

DETAILED DESCRIPTION OF A PREFERRED EMBODIMENT OF THE INVENTION

Figure 1:
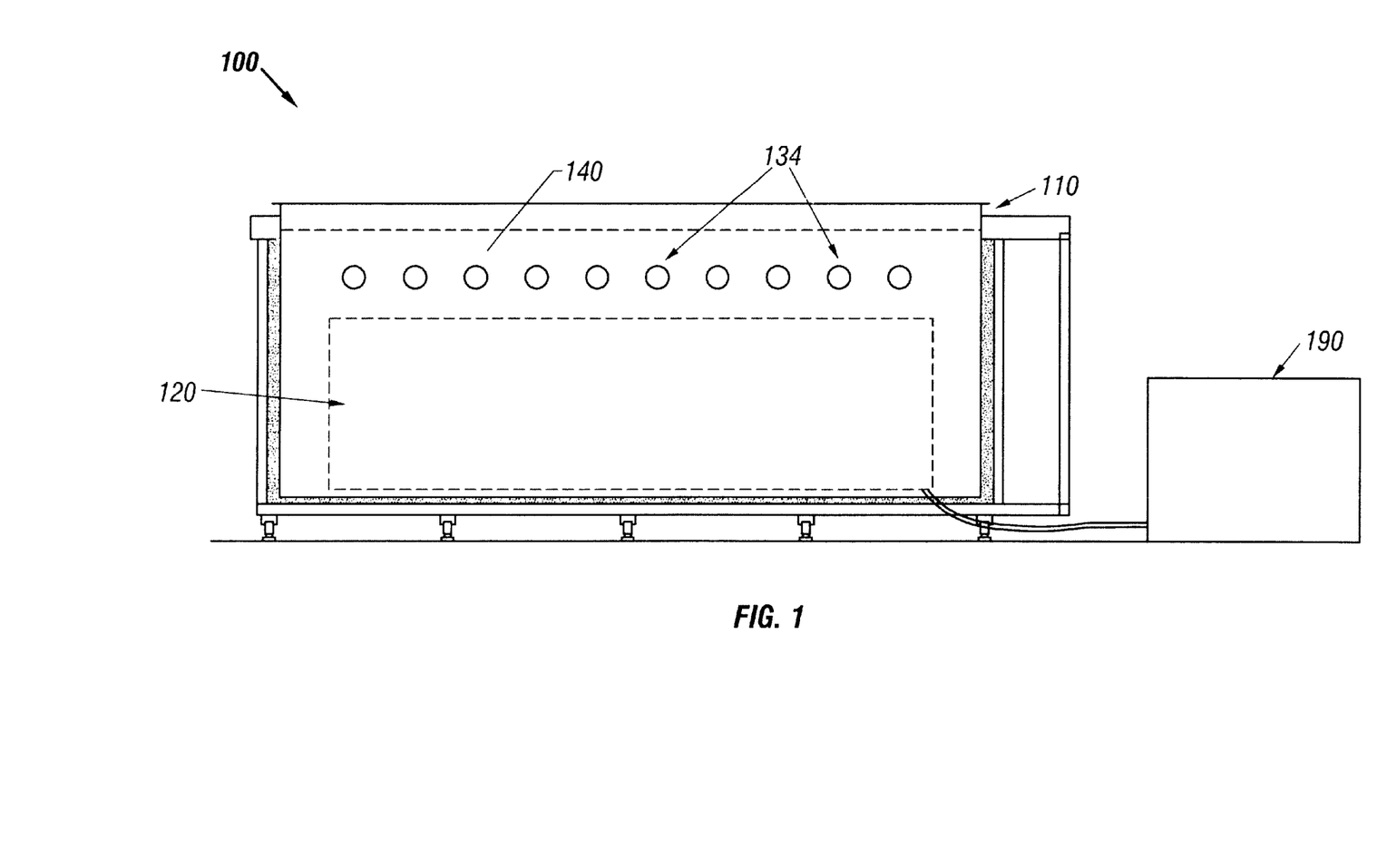
FIG. 1 is a side view of a chilling apparatus suitable for practicing a method according to at least one embodiment of the present invention.
Figure 2:
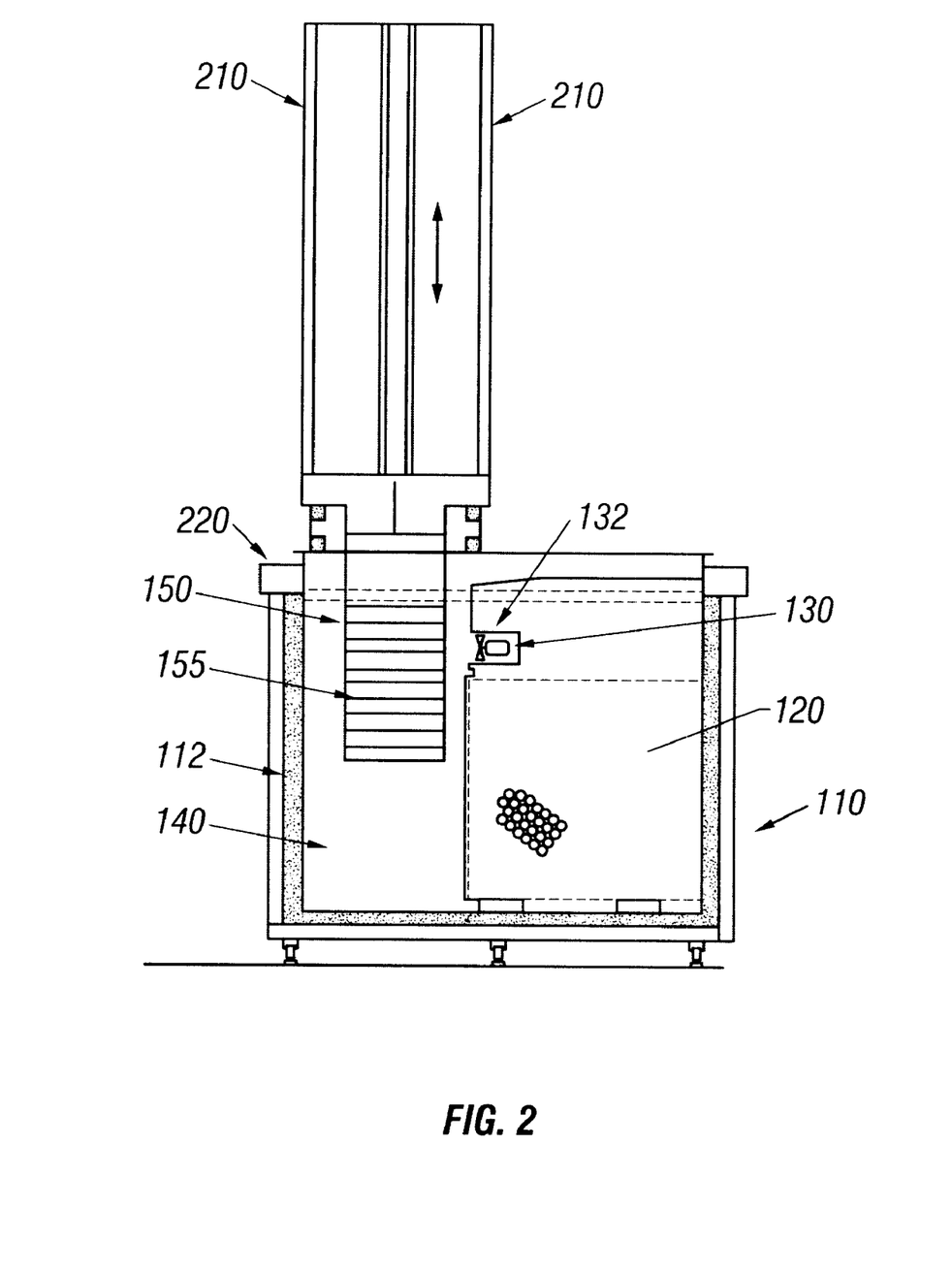
FIG. 2 is an end view of a cross-section of the chilling apparatus illustrated in FIG. 1.

Referring first to FIGS. 1 and 2, a chilling apparatus suitable for practicing a method according to at least one embodiment of the present invention is discussed, and designated generally as cooling unit 100. Cooling unit 100 preferably comprises tank 110 containing cooling fluid 140. Submersed in cooling fluid 140 are circulators 134 such as motors 130 having impellers 132, heat exchanging coil 120, and rack 150, which in one embodiment comprises trays 155 for supporting biological material to be frozen. Biological material may include, but is not limited to, viable single cells, tissues and organs, nucleic acids, and other biologically active molecules. External to tank 110, and coupled to heat exchanging coil 120, is refrigeration unit 190.

Tank 110 may be of any dimensions necessary to immerse biological material to be frozen in a volume of cooling fluid 140, in which the dimensions are scaled multiples of 12 inches by 24 inches by 48 inches. Other size tanks may be employed consistent with the teachings set forth herein. For example, in one embodiment (not illustrated), tank 110 is sized to hold just enough cooling fluid 140, so containers, such as vials, test tubes, beakers, graduated cylinders or the like, can be placed in tank 110 for rapid freezing of suspensions including biological materials and cryoprotectants. In other embodiments, tank 110 is large enough to completely immerse entire organs and or organisms for rapid freezing. It will be appreciated that tank 110 can be made larger or smaller, as needed to efficiently accommodate various sizes and quantities of biological material to be frozen. As subsequently discussed, the biological material is preferably treated with a cryoprotectant prior to being immersed in tank 110.

Tank 110 holds cooling fluid 140. In one embodiment, the cooling fluid is a food grade solute. Good examples of food grade quality fluids are those based on propylene glycol, sodium chloride solutions, or the like. In another embodiment, the cooling fluid is itself a cryoprotectant such as dimethylsulfoxide (DMSO), ethylene glycol, propylene glycol, polyethylene glycol or the like. Note that in some instances the cryoprotectant is itself a food grade quality fluid. In other embodiments, other fluids, and preferably solutes, are used as cooling fluids. While various containers may be used to hold the biological material, some embodiments of the present invention provide for the biological material to be directly immersed in the cooling fluid for rapid and effective freezing. Such direct immersion may simplify the cryopreservation of some tissues and organs.

In order to freeze biological material while avoiding the formation of ice crystals, one embodiment of the present invention circulates cooling fluid 140 past the biological material to be frozen, at a relatively constant rate of 35 liters per minute for every foot of cooling fluid contained in an area not more than 24 inches wide by 48 inches deep. The necessary circulation is provided by one or more circulators 134, such as motors 130. In at least one embodiment of the present invention, submersed motors 130 drive impellers 132 to circulate cooling fluid 140 past biological material to be frozen. Other circulators 134, including various pumps (not illustrated), can be employed consistent with the objects of the present invention. At least one embodiment of the present invention increases the area and volume through which cooling fluid is circulated by employing at least one circulator 134 in addition to motors 130. In embodiments using multiple circulators 134, the area and volume of cooling fluid circulation are increased in direct proportion to each additional circulator employed. For example, in a preferred embodiment, one additional circulator is used for each foot of cooling fluid that is to be circulated through an area of not more than about 24 inches wide by 48 inches deep.

Preferably, motors 130 can be controlled to maintain a constant predetermined velocity of cooling fluid flow past the biological material to be preserved, while at the same time maintaining an even distribution of cooling fluid temperature within +/−5° C. at all points within tank 110. The substantially constant predetermined velocity of cooling fluid circulating past the biological material, provides a constant, measured removal of heat, which allows for the vitrification of the biological material during freezing. In one embodiment, cooling fluid properties, such as viscosity, temperature, etc., are measured and processed, and control signals are sent to motors 130 to increase or decrease the rotational speed or torque of impellers 132 as needed. In other embodiments, motors 130 are constructed to maintain a given rotational velocity over a range of fluid conditions. In such a case, the torque or rotational speed of impellers 132 imparted by motors 130 are not externally controlled. Of note is the fact that no external pumps, shafts, or pulleys are needed to implement a preferred embodiment of the present invention. Motors 130, or other circulators 134, are immersed directly in cooling fluid 140. As a result, cooling fluid 140 not only freezes biological material placed in tank 110, but cooling fluid 140 also provides cooling for motors 130.

Heat exchanging coil 120 is preferably a "multi-path coil," which allows refrigerant to travel through multiple paths (i.e. three or more paths), in contrast to conventional refrigeration coils in which refrigerant is generally restricted to one or two continuous paths. In addition, the coil size is in direct relationship to the cross sectional area containing the measured amount of the cooling fluid 140. For example, in a preferred embodiment, tank 110 is one foot long, two feet deep and four feet wide, and uses a heat exchanging coil 120 that is one foot by two feet. If the length of tank 110 is increased to twenty feet, then the length of heat exchanging coil 120 is also increased to twenty feet. As a result, heat exchanging coil 120 can be made approximately fifty percent of the size of a conventional coil required to handle the same heat load. Circulators 134 such as motors 130, circulate chilled cooling fluid 140 over biological material to be frozen, and then transport warmer cooling fluid to heat exchanging coil 120, which is submersed in cooling fluid 140. In at least one embodiment, heat exchanging coil 120 is so designed to remove not less than the same amount of heat from cooling fluid 140 as that removed from the biological material being frozen, thereby maintaining the temperature of cooling fluid 140 in a predetermined range. Heat exchanging coil 120 is connected to refrigeration unit 190, which removes the heat from heat exchanging coil 120 and the system.

In a preferred embodiment, refrigeration unit 190 is designed to match the load requirement of heat exchanging coil 120, so that heat is removed from the system in a balanced and efficient manner, resulting in the controlled, rapid freezing of a material. The efficiency of the refrigeration unit 190 is directly related to the method employed for controlling suction pressures by the efficient feeding of the heat exchange coil 120 and the efficient output of compressors used in refrigeration unit 190.

This methodology requires very close tolerances to be maintained between the refrigerant and cooling fluid 140 temperatures, and between the condensing temperature and the ambient temperature. These temperature criteria, together with the design of the heat exchange coil 120, allows heat exchange coil 120 to be fed more efficiently, which in turn allows the compressor to be fed in a balanced and tightly controlled manner to achieve in excess of twenty-five percent greater performance from the compressors than that which is accepted as the compressor manufacturer's standard rating.

Note that in the embodiment illustrated in FIG. 1, refrigeration unit 190 is an external, remotely located refrigeration system. However, in another embodiment (not illustrated), refrigeration unit 190 is incorporated into another section of tank 110. It will be appreciated that various configurations for refrigeration unit 190 may be more or less appropriate for certain configurations of cooling unit 100. For example, if tank 110 is extremely large, a separate refrigeration unit 190 may be desirable, while a portable embodiment may benefit from an integrated refrigeration unit 190. Such an integration is only made possible by the efficiencies achieved by implementing the principles as set forth herein, and particularly the use of a reduced-size heat exchanging coil.

By virtue of refrigeration unit 190 and heat exchanging coil 120, in a preferred embodiment, the cooling fluid is cooled to a temperature of between −20° C. and −30°C., with a temperature differential throughout the cooling fluid of less than about +/−5° C. In other embodiments, the cooling fluid is cooled to temperatures outside the −20° C. to −30° C. range in order to control the rate at which a substance is to be frozen. Other embodiments control the circulation rate of the cooling fluid to achieve desired freezing rates. Alternatively, the volume of cooling fluid may be changed in order to facilitate a particular freezing rate. It will be appreciated that various combinations of cooling fluid circulation rate, cooling fluid volume, and cooling fluid temperature can be used to achieve desired freezing rates.

Referring now to FIG. 2, an embodiment of cooling system 100 suitable for freezing relatively large quantities of biological material is discussed. Reference numerals in FIG. 2 that are like, similar or identical to reference numerals in FIG. 1 indicate like, similar or identical features. Tank 110 contains cooling fluid 140, into which rack 150 may be lowered. Rack 150 is movably coupled to rack support 210, such that rack 150 may be raised or lowered to facilitate the placement of substances into tank 110.

In use, biological material to be frozen is placed in trays 155 of rack 150. Preferably, trays 155 are constructed of wire, mesh, or otherwise, so that cooling fluid 140 may freely circulate over, under and/or around items placed thereon. Preferably, once the cooling fluid is chilled to a desired temperature, rack support 210 lowers rack 150 into tank 110, in order to submerge trays 155 in cooling fluid 140. Lowering rack 150 may be accomplished manually or using various gear, chain, and/or pulley configurations known to those skilled in the art. Circulators 134 circulate cooling fluid 140 across substances placed in trays 155 to provide quick and controlled freezing. It will be appreciated that other arrangements for immersing biological material into tank 110 may be employed, and that use of an automatic lowering system is not necessarily preferred for use in all circumstances.

Figure 3:
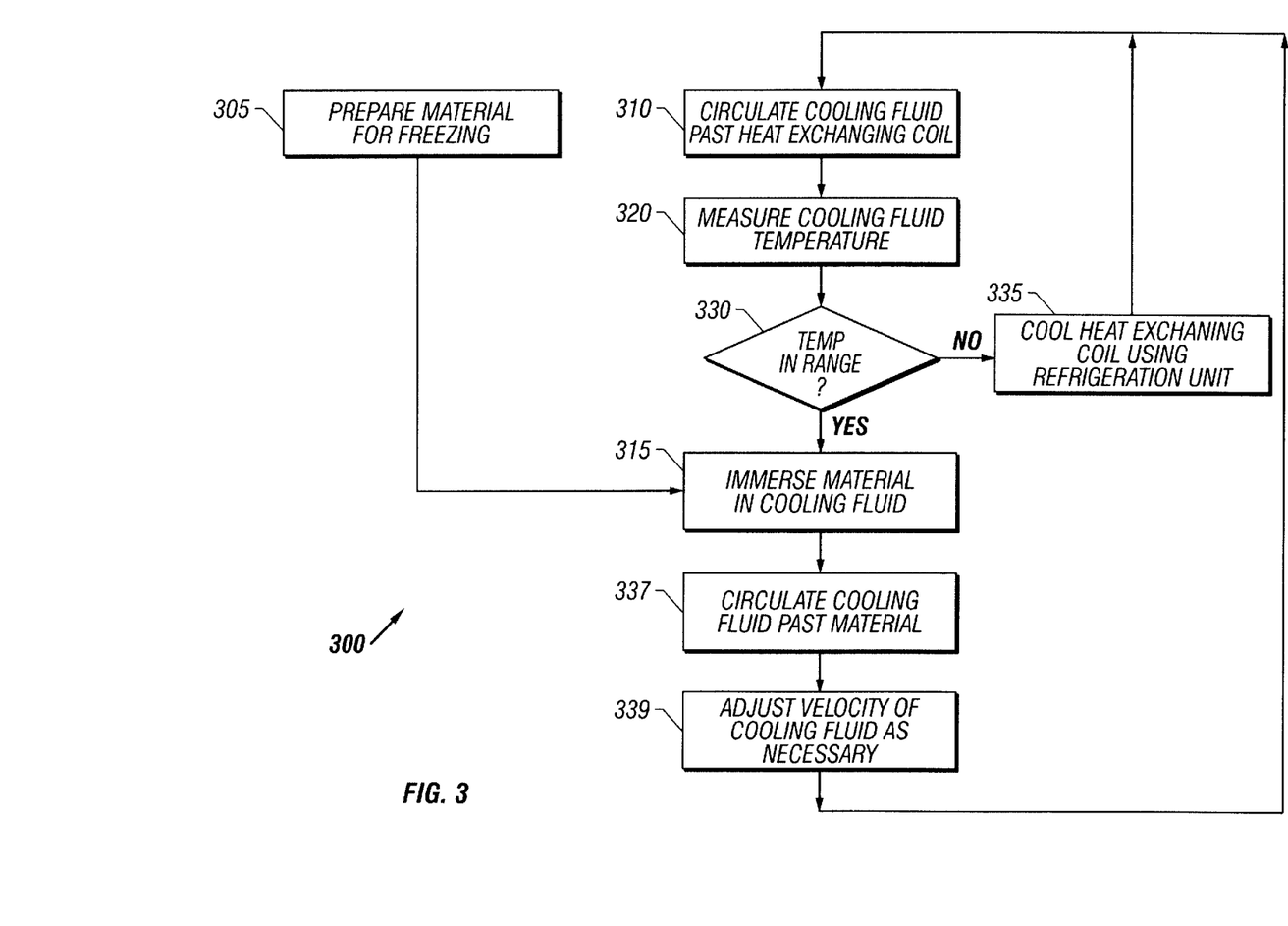
FIG. 3 is a flow diagram illustrating a method according to at least one embodiment of the present invention.

Referring now to FIG. 3, a method according to one embodiment of the present invention is illustrated, and designated generally by reference numeral 300. The illustrated method begins at step 310, where cooling fluid is circulated past a heat exchange coil. The heat exchange coil is operably coupled to a refrigeration system as discussed above, and is used to reduce the temperature of the cooling fluid as the cooling fluid is circulated past the heat exchange coil. In step 320, the temperature of the cooling fluid is measured, and the method proceeds to step 330 where it is determined whether the temperature of the cooling fluid is within an optimal temperature range. This optimal cooling fluid temperature range may be different for different applications, however, a preferred optimal temperature range for many applications is between −20° C. and −30° C.

If the cooling fluid temperature is determined not to be within an optimal, predetermined temperature range, step 335 is performed. In step 335, the heat exchanging coil is cooled by a refrigeration unit, and the method returns to step 310, in which the cooling fluid is circulated past the heat exchange coil in order to lower the temperature of the cooling fluid. Preferably, steps 310, 320, 330 and 335 are performed continually until the cooling fluid reaches the optimal temperature range.

The temperature of the cooling fluid used to freeze the biological material is an important element of at least one embodiment of the present invention. In order to achieve vitrification using conventional processes, biological material is generally quenched in liquid nitrogen, having a temperature of −196° C. Such a drastic change in temperature over a very short period of time freezes water within cell structures so quickly that ice crystals do not have a chance to form. However, freezing biological material by quenching in liquid nitrogen can cause stress fractures in cell membranes, thereby limiting the usefulness of quenching in liquid nitrogen for cryopreservation. Since the temperatures used in a preferred embodiment of the present invention are between −20° C. and −30° C., stress fractures due to temperature change are minimized, and vitrification can be achieved with far less damage to cell membranes.

While the cooling fluid is being cooled to the proper temperature, biological materials to be frozen are prepared for freezing in step 305. As noted earlier, biological material includes, but is not limited to, viable single cells, tissues and organs, nucleic acids and other biologically active molecules. Where appropriate, materials will undergo chemical preparation prior to freezing. Chemically preparing the biological material may include pretreatment of the biological material with agents (stabilizers) that increase cellular viability by removing harmful substances secreted by the cells during growth or cell death. Useful stabilizers include those chemicals and chemical compounds, many of which are known to those skilled in the art, which sequester highly reactive and damaging molecules such as oxygen radicals.

Chemically preparing biological material may also include an acclimation step (not illustrated). During or at some time after pretreatment, the biological material to be preserved may be acclimated to a temperature which is reduced from culturing temperatures, but still above freezing. This may help prepare the biological material for the cryopreservation process by retarding cellular metabolism and reducing the shock of rapid temperature transition. Note well, however, that an acclimation step is not always required in order to practice the present invention.

In a preferred embodiment, chemically preparing biological material for freezing includes loading the biological material with a cryoprotectant. Loading generally involves the equilibration of biological material in a solution of one or more cryoprotectants. Substances utilized during loading maybe referred to as loading agents. Useful loading agents may include one or more dehydrating agents, permeating and non-permeating agents, and osmotic agents. Both permeating agents such as DMSO and ethylene glycol, and a combination of permeating and non-permeating osmotic agents such as fructose, sucrose or glucose, and sorbitol, mannitol or glycerol can be used. It will be appreciated that other suitable cryoprotectants may be employed consistent with the objects of the present invention.

After the cooling fluid reaches a proper temperature, step 315 is performed, in which the chemically prepared biological material is immersed in cooling fluid. As noted earlier, the biological material may be held in a container, or placed directly into the cooling fluid. The method then proceeds to step 337, in which a circulator, such as a submersed motor/impeller assembly or pump, is used to circulate the cooling fluid at the velocity previously discussed, past the immersed biological material. As the cooling fluid passes by the biological material, heat is removed from the material, which is at a higher temperature than the temperature of the cooling fluid, and is transferred to the cooling fluid, which transports the heat away from the biological material to be frozen. According to at least one embodiment of the present invention, a substantially constant circulation of cooling fluid past the biological material to be frozen should be maintained in order to freeze the prepared biological material such that the prepared material is vitrified.

After the cooling fluid is circulated past the biological material to be frozen, step 339 is performed. Step 339 adjusts the velocity of the cooling fluid as necessary to account for changes in the cooling fluid viscosity, temperature, and the like. Preferably, the velocity of the cooling fluid is held constant by adjusting the force provided by one or more circulators.

The steps illustrated in FIG. 3 are shown and discussed in a sequential order. However, the illustrated method is of a nature wherein some or all of the steps are continuously performed, and may be performed in a different order. For example, at least one embodiment of the present invention uses a single circulating motor to circulate the cooling fluid. In such an embodiment, cooling fluid is circulated past a heat exchanging coil as in step 310 and past the biological material to be preserved in step 337 at the same time. In addition, one embodiment of the present invention measures cooling fluid temperatures, viscosities and other fluid properties continually, and at multiple locations within the system.

In yet another embodiment, some properties of the cooling fluid are not directly measured. Rather, the change in cooling fluid properties is determined indirectly from the rotational speed of a circulation motor. If the motor is turning at a slower rate, then additional power can be supplied to the motor to return the motor to the desired rotational speed, thereby compensating for the change in cooling fluid properties. In at least one embodiment, a motor is configured to maintain a substantially constant rate of rotation. This substantially constant rate of motor rotation will result in a substantially constant rate of cooling fluid circulation.

A test of one embodiment of the present invention was performed in which 5 ml of water was frozen in a graduated container. Upon freezing, there was less than one percent increase in total volume, much less than expected with conventional freezing. In another test, ice was frozen in sheets in a conventional freezer, and in a cooling system according to a preferred method of the present invention. After freezing, the ice was examined under dark microscope. As expected, the conventional ice displayed a crystalline pattern, whereas the ice frozen according to the principles of the present invention exhibited no light displacement, indicating little to no ice crystal formation.

Figure 4:
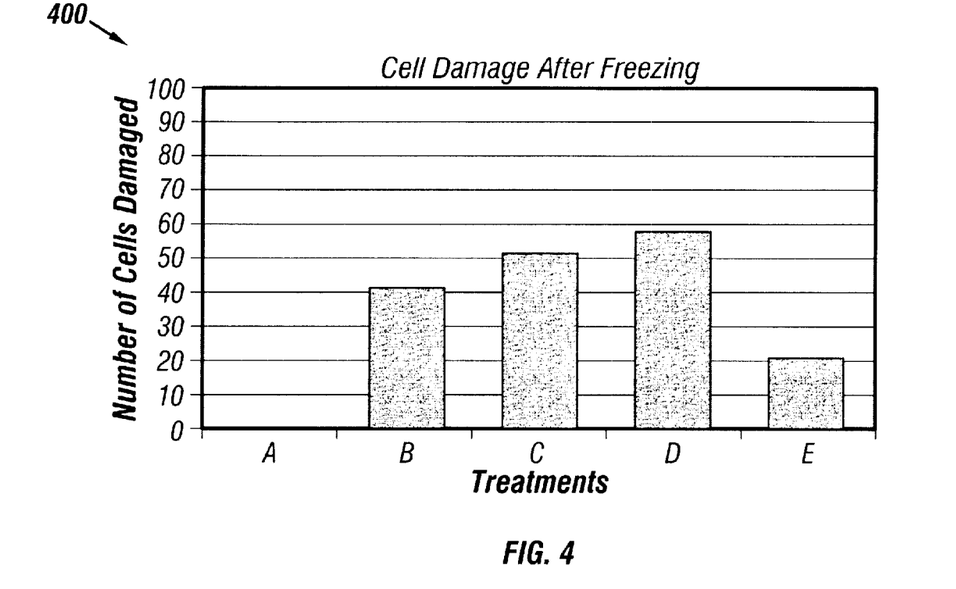
FIG. 4 is a bar chart showing the results of experimental comparisons of cellular damage in cross-sections of whole seedless grapes frozen without chemical preparation between various conventional freezers (not all of which are used for cryopreservation and storage) and a freezing method according to a preferred embodiment of the present invention.

Refer now to FIG. 4, in which experimental results comparing cellular damage following freezing of non-prepared plant tissue (whole, seedless grapes) utilizing a number of freezing methods are illustrated. Bar graph 400 compares the number of individual cells damaged by using methods B, C, D and E against a control group A. Method A was a fresh, never frozen control, method B used a conventional freezer to freeze to a temperature of −10° C., method C used an ultralow freezer to freeze cells to a temperature of −80° C., method D used liquid nitrogen to freeze cells to a temperature of −196° C., and method E used a preferred embodiment of the present invention to freeze cells to a temperature of −25° C.

The experiment, the results of which are shown in bar graph 400, used data from non-prepared, no cryoprotectant treated plant tissue. The results, as illustrated in FIG. 4, clearly show the superiority of the method performed according to a preferred embodiment of the present invention. None of the cells examined from the control, method A, exhibited any damage, so damage seen in other methods was due solely to freezing methodology. According to the test, 40 percent of the cells frozen using method B (conventional freezing) were damaged after thawing, approximately 50 percent of the cells were damaged following freezing and thawing with method C (ultralow freezer), and approximately 60 percent of the cells were damaged following freezing and thawing with method D (liquid nitrogen). Significantly, only 20 percent of the cells frozen with method E (a preferred embodiment of the present invention) were damaged upon thawing. Note that damage was assessed by examining the plant cell wall under magnification.

Figure 5:
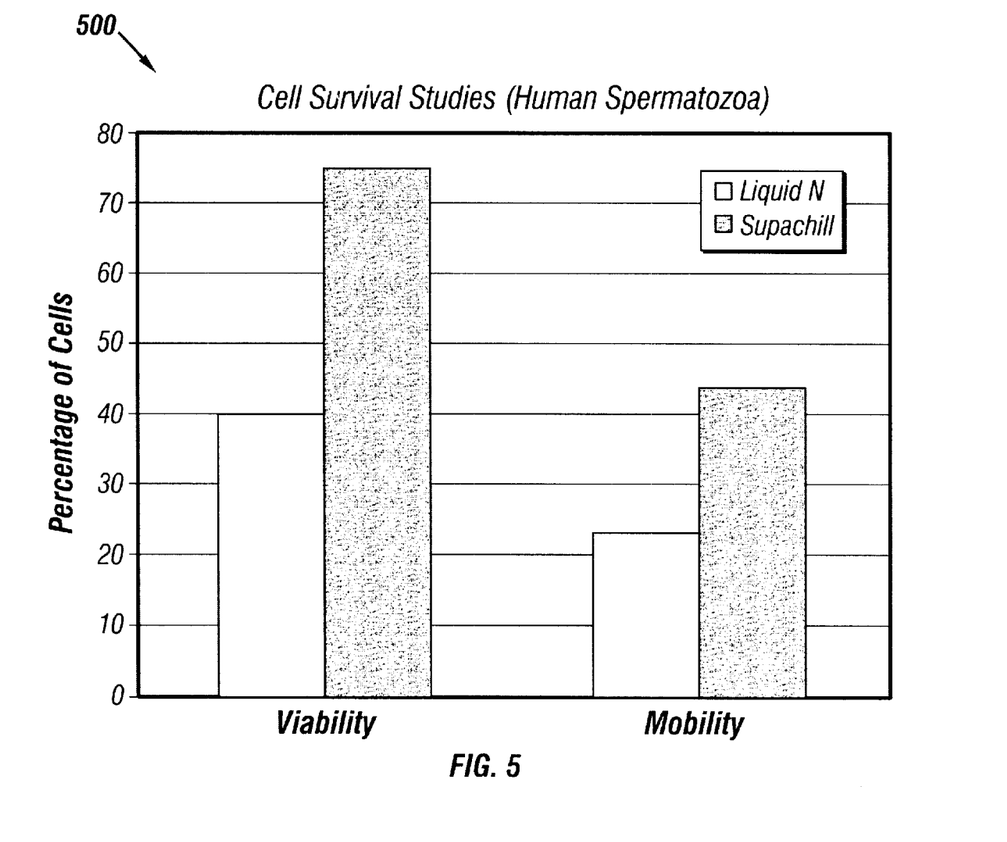
FIG. 5 is a bar chart showing results of experimental comparisons of cell survival and function post-thaw of human spermatozoa between a prior art freezing method and a freezing method according to a preferred embodiment of the present invention.

Refer now to FIG. 5, in which experimental results of cell survival (viability) and cell function, measured as cell motility, following freezing of chemically prepared human spermatozoa cells comparing a prior art freezing method and a freezing method according to a preferred embodiment of the present invention. Cells for both methods were chemically prepared for freezing using an industry standard technique. Bar graph 500 compares cell viability and motility following freezing using the two methods. Method A used a conventional method of suspending cells in nitrogen mist for 30 minutes and then plunging the cells into liquid nitrogen. Method B used a preferred embodiment of the present invention to freeze cells to a temperature of −25° C.

The experiment, which results are shown in bar graph 500, used chemically prepared human spermatozoa. The results illustrated by bar graph 500 clearly show the superiority of the method performed according to a preferred embodiment of the present invention. According to the test, only 40 percent of the cells frozen using method A (conventional method) remained viable upon thaw and only approximately 20 percent of the cells maintained their motility. However, 75 percent of the cells frozen using method B were viable on thaw, and approximately 45 percent of the cells were still motile. Note that viability of the cells was assessed using a live-dead stain upon thaw, and motility was determined by direct observation fo the cells under magnification.

Figure 6:
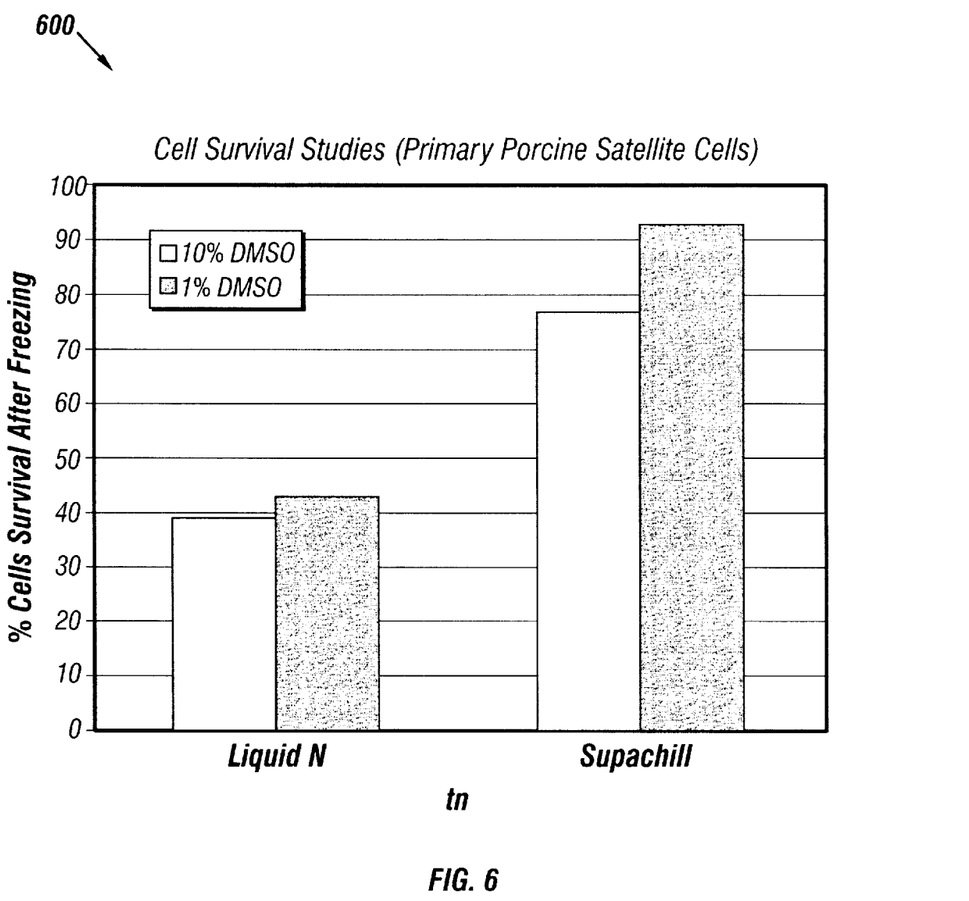
FIG. 6 is a bar chart showing results of experimental comparisons of cell survival post-thaw of porcine muscle cells between a prior art freezing method and a freezing method according to a preferred embodiment of the present invention.

Refer now to FIG. 6, in which experimental results of cell survival (viability) following freezing of chemically prepared porcine muscle cells comparing a prior art freezing method and a freezing method according to a preferred embodiment of the present invention. Cells for both methods were chemically prepared for freezing using two concentrations of cryoprotectants. Bar graph 600 compares cell viability following freezing for each of the methods. Method A uses a 10 percent concentration of cryoprotectant coupled with the conventional method of plunging the cells into liquid nitrogen, method B uses a 1 percent concentration of cryoprotectant coupled with the conventional method of plunging the cells into liquid nitrogen. Method C uses a 10 percent concentration of cryoprotectant coupled with a preferred embodiment of the present invention to freeze cells to a temperature of −25° C., and method D uses a 1 percent concentration of cryoprotectant coupled with a preferred embodiment of the present invention to freeze cells to a temperature of −25° C.

The experiment, which results are shown in bar graph 600, used chemically prepared porcine muscle cells. The results of the experiment, as illustrated in FIG. 6, clearly show the superiority of the method performed according to a preferred embodiment of the present invention. According to the test, approximately 40 percent of the cells frozen using either methods A (conventional methods with 10 percent cryoprotectant) or B (conventional methods with 1 percent cryoprotectant) remained viable upon thaw. However, over 80 percent of cells frozen using either methods C (a preferred embodiment of the present invention with 10 percent cryoprotectant) or D (a preferred embodiment of the present invention with 1 percent cryoprotectant) were viable on thaw. Note that the viability of the cells was assessed using a live-dead stain upon thaw.

Figure 7:
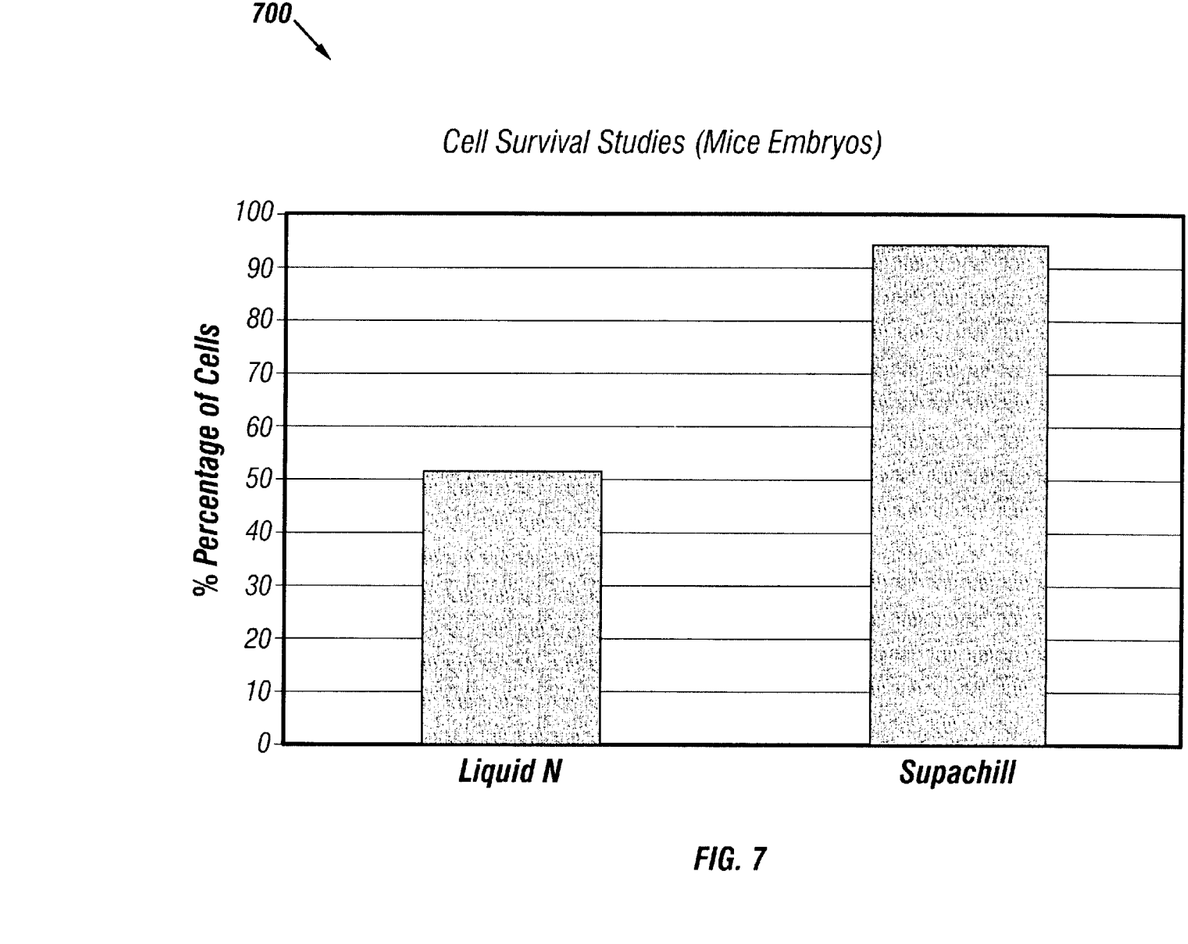
FIG. 7 is a bar chart showing results of experimental comparisons of cell survival of mice embryos between a prior art freezing method and a freezing method according to a preferred embodiment of the present invention.

Refer now to FIG. 7, in which experimental results of cell survival (viability) following freezing of chemically prepared mice embryos comparing a prior art freezing method and a freezing method according to a preferred embodiment of the present invention. Cells for both methods were chemically prepared for freezing using an industry standard technique. Bar graph 700 compares embryo viability following freezing using the two methods. Method A used a conventional method of controlled rate freezing in nitrogen mist followed by plunging the embryos into liquid nitrogen. Method B used a preferred embodiment of the present invention to freeze cells to a temperature of −25° C. followed by plunging into liquid nitrogen.

The experiment, which results are shown in bar graph 700, used data from chemically prepared mice embryos. The results as illustrated in FIG. 7, clearly show the superiority of the method performed according to a preferred embodiment of the present invention. According to the test, only approximately 50 percent of the embryos frozen using method A (conventional method) remained viable upon thaw. However, over 90 percent of the embryos frozen using method B were viable on thaw. Note that viability of the embryos was assessed using a live-dead stain upon thaw.

Because the present invention can freeze biological material such that the material is vitrified and the formation of stress fractures in cell membranes is minimized, various embodiments of the present invention may find application in medical areas such as skin grafts, cornea storage, circulatory vessel storage, freezing of transplant tissues, infertility treatment, and the investigation of molecular regeneration disease (cancer). Alternatively, the present invention may find use in the livestock industry for cryopreservation of semen, oocytes and embryos.

In the preceding detailed description, reference has been made to the accompanying drawings which form a part hereof, and in which are shown by way of illustration specific embodiments in which the invention may be practiced. These embodiments have been described in sufficient detail to enable those skilled in the art to practice the invention, and it is to be understood that other embodiments may be utilized and that logical, mechanical, chemical and electrical changes may be made without departing from the spirit or scope of the invention. To avoid detail not necessary to enable those skilled in the art to practice the invention, the description omits certain information known to those skilled in the art. The preceding detailed description is, therefore, not to be taken in a limiting sense, and the scope of the present invention is defined only by the appended claims.

What is claimed is:

1. A method of cryopreservation comprising:
   immersing biologically active material in cooling fluid; and
   circulating the cooling fluid past the biologically active material at a substantially constant predetermined velocity and temperature to freeze the biologically active material such that the biologically active material is vitrified, and the formation of stress fractures in cell membranes is minimized.

2. The method as in claim 1, wherein the cooling fluid is maintained at a temperature of between about −20 degrees centigrade and −30 degrees centigrade.

3. The method as in claim 1, wherein the velocity of the cooling fluid past the biologically active material is about 35 liters per minute per foot of cooling fluid through an area not greater than about 24 inches wide and 48 inches deep.

4. The method a s in claim 1, further comprising chemically preparing the biologically active material for freezing.

5. The method as in claim 4, wherein chemically preparing the biologically active material for freezing includes treating the material with a cryoprotectant.

6. The method as in claim 1, wherein the cooling fluid is circulated by a circulator immersed in the cooling fluid.

7. The method as in claim 6, wherein the circulator comprises:
   a motor; and
   an impeller rotatably coupled to the motor such that the impeller rotates to circulate the cooling fluid.

8. The method as in claim 1, further comprising circulating the cooling fluid past a heat exchanging coil submersed in the cooling fluid, and wherein the heat exchanging coil is capable of removing at least the same amount of heat from the cooling fluid, as the cooling fluid removes from the biologically active material.

9. The method as in claim 8, wherein the heat exchanging coil is a multi-path coil.

10. The method as in claim 8, wherein the size of the heat exchanging coil is directly related to an area through which the cooling fluid is circulated, wherein the area is about 24 inches wide and 48 inches deep.

11. The method as in claim 8, further comprising cooling the heat exchanging coil with a refrigeration unit substantially matching load requirements of the heat exchanging coil.

12. The method as in claim 1, wherein the biologically active material comprises viable single cells.

13. The method as in claim 1, wherein the biologically active material comprises viable tissues.

14. The method as in claim 1, wherein the biologically active material comprises viable organs.

15. The method as in claim 1, wherein the biologically active material comprises viable nucleic acids.

16. The method as in claim 1, wherein the biologically active material comprises viable ribonucleic acids.

17. The method as in claim 1, wherein the biologically active material comprises viable amino acid based compounds.

18. The method as in claim 1, wherein the biologically active material comprises viable lipid based compounds.

19. A method of cryopreservation comprising;
   immersing biologically active material in cooling fluid; and
   freezing the biologically active material directly to a temperature higher than about −30 degrees centigrade by circulating the cooling fluid past the biologically active material at a substantially constant predetermined velocity and temperature such that the biologically active material is vitrified.

20. The method as in claim 19, wherein the cooling fluid is maintained at a temperature of between about −20 degrees centigrade and −30 degrees centigrade.

21. The method as in claim 19, wherein the velocity of the cooling fluid past the biologically active material is about 35 liters per minute per foot of cooling fluid through an area not greater than about 24 inches wide and 48 inches deep.

22. The method as in claim 19, further comprising chemically preparing the biologically active material for freezing.

23. The method as in claim 22, wherein chemically preparing the biologically active material for freezing includes treating the biologically active material with a cryoprotectant.

24. The method as in claim 19, wherein the cooling fluid is circulated by a circulator immersed in the cooling fluid.

25. The method as in claim 24, wherein the circulator comprises:
   a motor; and
   an impeller rotatably coupled to the motor such that the impeller rotates to circulate the cooling fluid.

26. The method as in claim 19, further comprising circulating the cooling fluid past a heat exchanging coil submersed in the cooling fluid, and wherein the heat exchanging coil is capable of removing at least the same amount of heat from the cooling fluid, as the cooling fluid removes from the biologically active material.

27. The method as in claim 26, wherein the heat exchanging coil is a multi-path coil.

28. The method as in claim 26, wherein the size of the heat exchanging coil is directly related to an area through which the cooling fluid is circulated, wherein the area is about 24 inches wide and 48 inches deep.

29. The method as in claim 26, further comprising cooling the heat exchanging coil with a refrigeration unit substantially matching load requirements of the heat exchanging coil.

30. The method as in claim 19, wherein the biologically active material comprises viable single cells.

31. The method as in claim 19, wherein the biologically active material comprises viable tissues.

32. The method as in claim 19, wherein the biologically active material comprises viable organs.

33. The method as in claim 19, wherein the biologically active material comprises viable nucleic acids.

34. The method as in claim 19, wherein the biologically active material comprises viable ribonucleic acids.

35. The method as in claim 19, wherein the biologically active material comprises viable amino acid based compounds.

36. The method as in claim 19, wherein the biologically active material comprises viable lipid based compounds.

37. A biological material having been subjected to a cryopreservation process, the cryopreservation process comprising:
   immersing the biological material in cooling fluid; and
   circulating the cooling fluid past the biological material at a substantially constant predetermined velocity and temperature to freeze the biological material such that the biological material is vitrified, and the formation of stress fractures in cell membranes is minimized.

38. The biological material as in claim 37, wherein the cooling fluid is maintained at a temperature of between about −20 degrees centigrade and −30 degrees centigrade.

39. The biological material as in claim 37, wherein the velocity of the cooling fluid past the prepared material is about 35 liters per minute per foot of cooling fluid through an area not greater than about 24 inches wide and 48 inches deep.

40. The biological mat e rial as in claim 37, wherein said cryopreservation process further includes chemically preparing the biological material for freezing.

41. The biological material as in claim 40, wherein chemically preparing the biological material for freezing includes treating the material with a cryoprotectant.

42. The biological material as in claim 37, wherein the cooling fluid is circulated by a circulator immersed in the cooling fluid.

43. The biological material as in claim 42, wherein the circulator comprises:
   a motor; and
   an impeller rotatably coupled to the motor such that the impeller rotates to circulate the cooling fluid.

44. The biological material as in claim 37, wherein the cryopreservation process further comprises circulating the cooling fluid past a heat exchanging coil submersed in the cooling fluid, and wherein the heat exchanging coil is capable of removing at least the same amount of heat from the cooling fluid, as the cooling fluid removes from the biological material.

45. The biological material as in claim 44, wherein the heat exchanging coil is a multi-path coil.

46. The biological material as in claim 44, wherein the size of the heat exchanging coil is directly related to an area through which the cooling fluid is circulated, wherein the area is about 24 inches wide and 48 inches deep.

47. The biological material as in claim 44, further comprising cooling the heat exchanging coil with a refrigeration unit substantially matching load requirements of the heat exchanging coil.

48. The biological material as in claim 37, wherein said biological material comprises viable single cells.

49. The biological material as in claim 37, wherein said biological material comprises viable tissues.

50. The biological material as in claim 37, wherein said biological material comprises viable organs.

51. The biological material as in claim 37, wherein said biological material comprises viable nucleic acids.

52. The biological material as in claim 37, wherein the biological material comprises viable ribonucleic acids.

53. The biological material as in claim 37, wherein the biological material comprises viable amino acid based compounds.

54. The biological material as in claim 37, wherein the biological material comprises viable lipid based compounds.

* * * * *